United States Patent [19]

Lares et al.

[11] Patent Number: 4,611,990
[45] Date of Patent: Sep. 16, 1986

[54] DENTAL HANDPIECE CONSTRUCTION

[75] Inventors: Joseph P. Lares, Redwood City; Mark Cowell, San Carlos, both of Calif.

[73] Assignee: Lares Research, San Carlos, Calif.

[21] Appl. No.: 691,142

[22] Filed: Jan. 14, 1985

[51] Int. Cl.⁴ .............................................. A61C 1/14
[52] U.S. Cl. .................................... 433/129; 279/123
[58] Field of Search ................ 433/129, 132; 279/123, 279/46

[56] References Cited

U.S. PATENT DOCUMENTS

| 1,812,144 | 6/1931 | Earl | 279/46 |
| 2,161,939 | 6/1939 | Sutton | 279/46 |
| 2,214,241 | 9/1940 | Baxendale | 279/46 |
| 2,689,740 | 9/1954 | Parigian | 279/46 |
| 2,895,738 | 7/1959 | Baker | 433/129 |
| 3,074,167 | 1/1963 | Turchi et al. | 433/129 |
| 3,314,153 | 4/1967 | Maurer | 433/129 |
| 4,436,512 | 3/1984 | Garcia | 433/129 |
| 4,493,645 | 1/1985 | Nakanishi | 433/129 |

FOREIGN PATENT DOCUMENTS 2905484  8/1979  Fed. Rep. of Germany ...... 433/129

Primary Examiner—Robert Peshock
Attorney, Agent, or Firm—Lothrop & West

[57] ABSTRACT

A dental handpiece grips a removable dental tool by teeth within the end of a resilient quill carried within the spindle of said handpiece and when rotated in one direction by the handpiece turbine providing an axial force on the dental tool tending to draw the tool axially into the quill despite any opposite pull due to teeth on the dental tool.

3 Claims, 5 Drawing Figures

DENTAL HANDPIECE CONSTRUCTION

BRIEF SUMMARY OF THE INVENTION

A dental handpiece has a housing carrying a turbine-driven hollow spindle mounted for rotation in one direction about an axis. A removable quill within the spindle acts as a chuck and has internal teeth engaging the shaft of a dental tool. The teeth are inclined in a direction to tend to draw the tool shaft into the quill when the tool is working; i.e. is rotated under load. The inclination of the quill teeth is opposite to the inclination of the working teeth on the tool itself.

PRIOR ART AND INFORMATION DISCLOSURE

Dental handpieces of the kind disclosed herein are representatively shown in Lares et al. U.S. Pat. No. 4,146,964 dated April 3, 1974 and entitled "Dental Handpiece".

DETAILED DESCRIPTION

Figure 1:
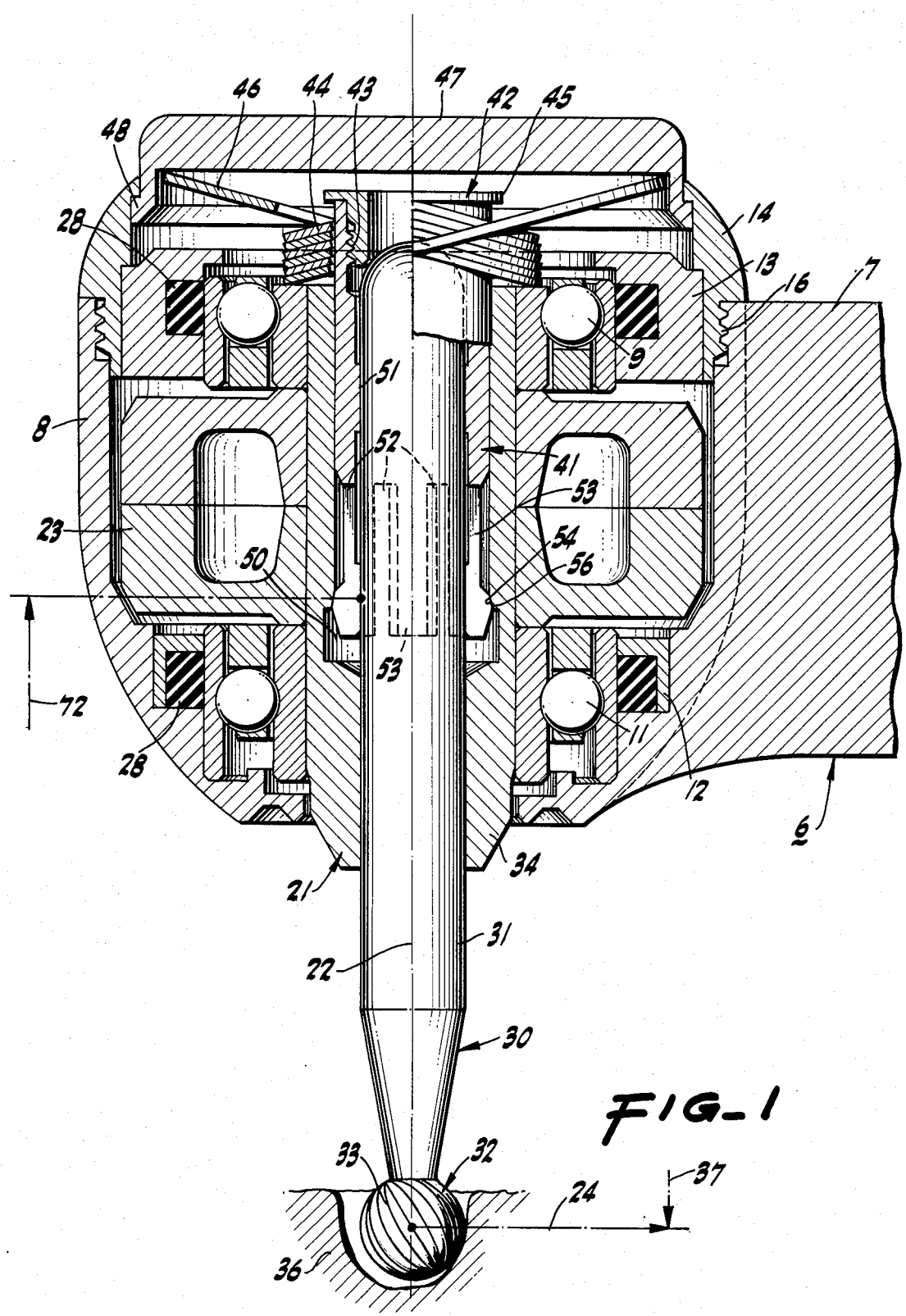
FIG. 1 is a cross-section on an axial plane through the operating or chuck end of a dental handpiece constructed to utilize the invention of this disclosure and showing an operating tool and its environment.
Figure 5:
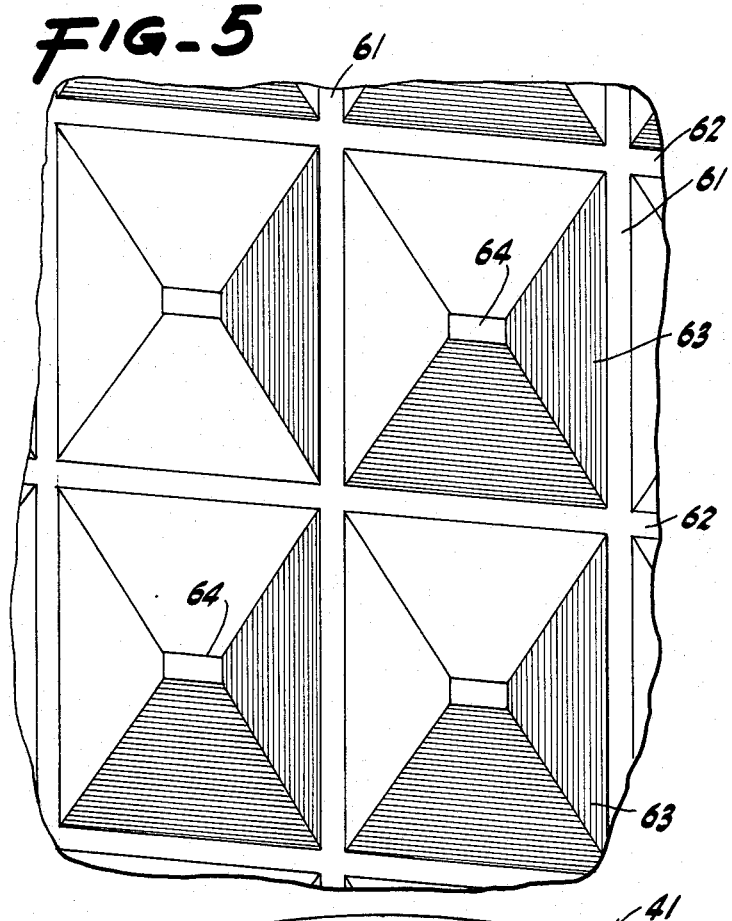
FIG. 5 is a detail showing in elevation the interior surface construction of a portion of the quill, the area illustrated being outlined in FIG. 3 by a broken line labeled 5.
Figure 3:
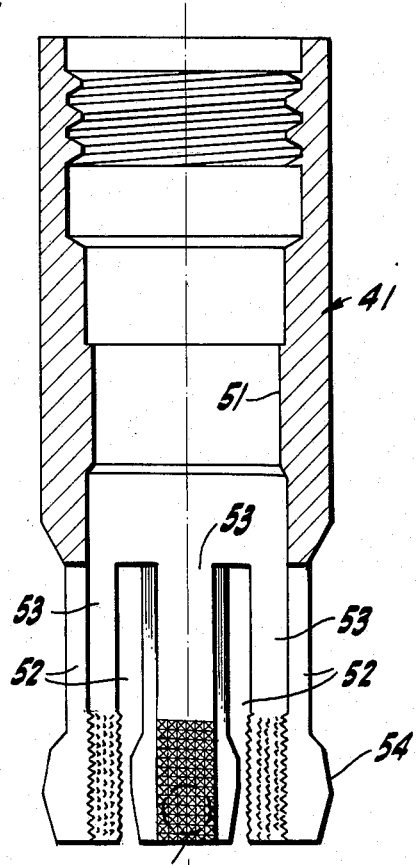
FIG. 3 is a cross-section, the plane of which is indicated by the line 3—3 of FIG. 2.
Figure 4:
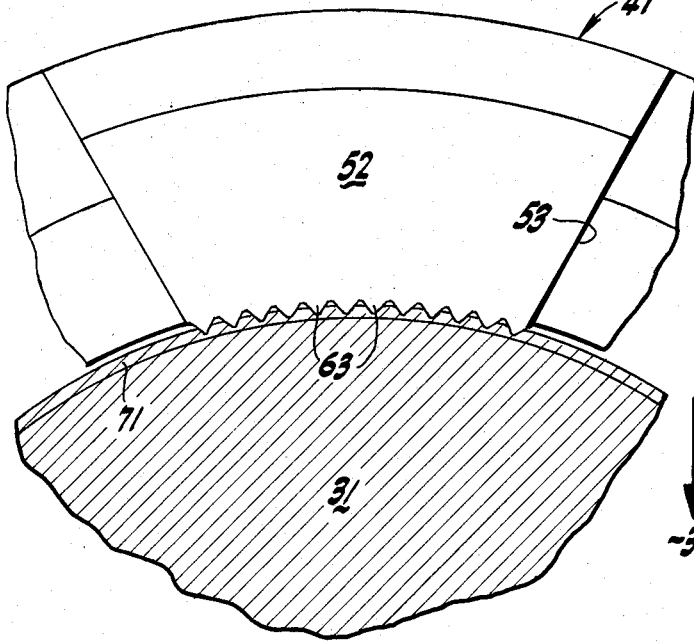
FIG. 4 is a cross-section, like FIG. 2, but to a greatly enlarged scale and with various portions broken away to reduce the size of the figure.
Figure 2:
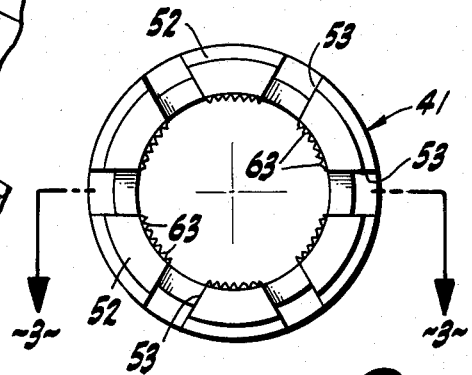
FIG. 2 is an end view of a quill utilized within the hollow spindle of the handpiece.

While the arrangement of the invention can be embodied in many different ways and can be applied in connection with different sorts of dental handpieces as well as other comparable rotary tools, it has with success been embodied as shown herein utilizing a dental handpiece 6 of the type shown in the above-mentioned Lares et al. patent. This device includes an operating handle 7 leading to a housing 8 made up of several parts. The housing carries anti-friction bearings 9 and 11 including suitable races. The lower bearing 11 is mounted in a support ring 12 seated in the housing. The upper bearing 9 is disposed in a support ring 13 seated in a carrier 14 forming part of and removably engaging the remainder of the housing 8 through a threaded connection 16.

The bearings 9 and 11 support a hollow spindle 21 for rotation about an axis 22 and about which the parts are symmetrical. A turbine runner 23, preferably made in two abutting halves, is tightly mounted on the hollow spindle between the bearings 9 and 11 and receives driving air through jet orifices (not shown). The turbine is driven in either one of two opposite directions, the one chosen for illustration being a predetermined direction indicated by the vector arrow 24 near the bottom of FIG. 1. This is clockwise when looking toward the turbine from the bottom or tool end of FIG. 1. The hollow spindle 21 is mounted in the bearings 9 and 11 so that the spindle can revolve very freely about the axis 22 (some 400,000–500,000 r.p.m.), but the spindle cannot move axially. The mountings of the bearings, including the carrier rings 12 and 13, although permitting some vibration (dampened by inserted elastic rings 28) are sufficiently firm as to preclude relative end motion of the spindle 21.

A working tool 30 of the sort illustrated as an example has a shaft 31 and a globular end 32 with cutting teeth 33 thereon inclined as shown. The kinds of tool may vary both as to the nature and pitch and inclination of the teeth and as to the diameter of the shaft. The hollow spindle 21 has a lower hub 34 receiving the shaft 31 with an easy sliding fit. The direction of rotation and the angle of the teeth 33 are such, in the case illustrated, that when the teeth engage an adjacent material 36 to be cut, the work load not only imposes a rotary drag on the tool, but generates an axial force, represented by the vector arrow 37, acting in a direction tending to pull the shaft 31 out of the hollow spindle 21.

To afford an improved arrangement for the spindle and particularly to preclude any tendency to expel the tool shaft 31 from the handpiece, the spindle is made to receive a coaxial quill 41. This is disposed within the spindle 21 and projects through the open top of the spindle. The quill is provided at the top with a removable cap 42 having a threaded interengagement 43 with the hollow quill. The cap 42 acts as an approximate or an exact stop for the upper end of the tool 30. The cap 42 is also arranged to bear against the upper, inner rim of the uppermost one of a nest of bent springs 44 by reason of an outstanding cap flange 45. The bent springs are essentially annular washers dihedrally bent along one diameter. The lowermost one rests on the end of the inner race of the bearing 9. By this construction, the quill is mounted for small axial movement within and with respect to the hollow spindle, accompanied by deflection of the bent springs 44.

A single, larger bent spring 46 at its inner margin rests on the top of the support ring 13 and also rests at its outer margin within and against a plunger top 47. An outer confining flange 48 of the plunger top can move axially toward and away from a spun-over flange 49 on the removable carrier 14. This arrangement permits the plunger top 47 manually to be moved axially toward the hollow spindle against the flexure of the bent spring 46. Normally, the plunger top is spring-projected, but the springs are of only sufficient strength so that the plunger top 47 can easily be depressed even by a slight, dental assistant. The quill is finished laterally to provide an annular land 51 as a centering guide adjacent the upper end of the shaft 31.

Cut into the quill from one end is a number of axial slots 52. These go only part way along the quill to define a number (herein, six) of intervening fingers 53 each having resilience in its own particular radial direction. Each finger near its end has an external conical surface 54 disposed to mate with an internal conical surface 56 providing a step on the interior of the hollow spindle 21 leading from an enlarged chamber 50 on the inside of the spindle.

When the parts are substantially in the position shown in FIG. 1 with a tool shaft 31 in place and the plunger top 47 in its uppermost position, the acting spring forces tend to move the conical surfaces 54 axially upwardly against the conical surface 56. This tends to move the fingers 53 radially inwardly a small amount sufficient to engage the inside of the fingers with the adjacent surface of the tool shaft 31.

The bent springs 44, effective to urge the quill upwardly, could well be made strong enough to press the fingers 53 against the shank 31 with sufficient force to preclude axial and rotary slippage of the tool. But such spring forces are so large as to make release of the tool from the quill a difficult, awkward job for many dental assistants.

To alleviate this difficulty, the fingers 53, especially as shown in FIGS. 2, 3, 4 and 5, are uniquely finished on the interior. Each finger is provided with a number of axial scores 61 and a number of helical scores 62. These various scores intersect and define between them approximately rectangular tips 63. Preferably, these tips are formed by or are the result of turning and broaching. They amount to pyramids with inclined, flat faces terminating approximately to define a flat, approximately trapezoidal inner tip surface 64. The drawings are representative and are to different, exaggerated scales. The size of each flat or tip 64 is minute and is barely discernible with the naked eye. The helical grooves 62 are made with a general slant or incline in a direction opposite to the slant or incline of the teeth 33 on the standard, commercial tool 30. If one can be likened to a left-hand thread, the other is then like a right-hand thread.

The arrangement of the spindle 21 and of the quill 41 and its associated parts is such that, without any tool stem in place, the quill can easily be removed from its operating position. The carrier 14 can be unscrewed from the housing 8 and, with the support ring 13 and the plunger top 47, can be put to one side, leaving the bearing 9 in situ. The bent spring 46 can be lifted off with the top 47 lifted off by hand or can be left in place. By exerting an axial lifting force on the removable cap 42, the entire quill 41 is also lifted. Since there is no tool shaft in position, the lifting motion causes the fingers 53 to be cammed inwardly by the surfaces 54 and 56, and the entire quill is thus easily withdrawn from the spindle and, by a reverse series of operations, can as easily be repositioned or replaced with a different quill. In either case, the motion of the quill into the spindle is finally accompanied by a snapping motion of the fingers 53 into outward position, with the surfaces 54 and 56 properly in abutment and with the finger ends spread in position within the chamber 55.

In the operation of this structure, the user easily depresses the plunger top 47 to abut the cap 42, flex the springs 46 and 44 and displace the quill 41 axially downwardly or toward the tool end of the hollow spindle. This permits the springy fingers 53 to expand fully in radial directions into the annular space provided and to form a central opening between them larger than the outside diameter of the tool shaft 31. While the cap 47 is still depressed, an appropriate tool shaft is inserted substantially into the position shown in FIG. 1. Then the plunger top 47 is released and is restored to upper position by the spring 46. The effect of the bent springs 44 is to move the quill 41 upwardly in an axial direction and to slide the conical faces 54 upwardly against and over the cone 56. This moves the finger ends radially inwardly into engagement with the shaft 31 of the tool.

The turbine rotor can then be energized to turn all of the rotary parts about the axis 22. When the rotating tool end 32 is manipulated against the workpiece 36, especially laterally, the inclined teeth 33 thereon exert a force having a component tending to draw the tool shaft 31 out of the quill 41. But by the same token, the concurrent rotation of the quill fingers 53 exerts a force against the shaft 31 having a component tending to draw the stem shaft 31 into the quill 41. That is because of the interengagement of the inclined peaks or tips 64 with the outer material of the quill. Whether or not this is a layer 71 of plating or the like, the peaks or tips 64 tend firmly to engage and even to bite into the surface material. The peaks 64 are sufficiently inclined in a direction opposite to the direction of inclination of the teeth 33 on the tool 30 to result in a net force component, represented by the longer vector arrow 72, tending to draw the drill shaft 31 into the quill 41. The forces involved give a net inward force on the working tool so as to preclude outward motion of the tool.

When work and the turbine have been stopped, depression of the plunger top 47 again flexes the bent spring 46 and flexes the bent springs 44 and moves the quill 41 downwardly. This moves the conical surfaces 54 away from the cone 56. The quill lower end then expands due to its own springiness and frees the tool shaft 31. The tool can then easily be removed.

The result of this arrangement is to provide a net inward force on the working tool. The tool remains properly in position and is held without requiring any heavy spring force to afford a readily operated plunger top.

We claim:

1. A dental handpiece construction comprising a housing; a hollow spindle mounted in said housing for rotation about an axis; means in said housing for so rotating said spindle in a predetermined direction; means in said spindle for gripping a removable tool; said tool gripping means including an annular, integral quill slidably receivable coaxially within one end of said hollow spindle; means defining a first conical surface within said spindle converging toward said one end of said spindle; radially resilient fingers on said quill; and means defining on each of said resilient fingers a second conical surface adapted to engage said first conical surface and to pass through said hollow spindle toward and out of said one end thereof.

2. A dental handpiece construction comprising an open top hollow housing symmetrical about an axis, a carrier having a top opening and detachably engaging said housing, a plunger top axially slidable on said carrier and extending across said axis to close said top opening, a bearing in said housing and a bearing in said carrier, said bearings being concentric with said axis, a hollow integral spindle mounted in said housing and engaging said bearings for rotation about said axis, said spindle between the ends thereof having a chamber enlarged from said spindle bore to provide a step between the ends of said spindle, means in said housing for rotating said spindle about said axis, a hollow integral quill disposed coaxially within said hollow spindle and axially movable in said spindle, means for defining a plurality of radially resilient fingers on one end of said quill, said fingers having enlargements adapted in one axial position of said quill to be extended radially outwardly from said axis into said chamber and in another axial position of said quill to be disposed radially inwardly toward said axis for gripping a removable tool in said quill and absent said tool to pass axially over said step and entirely through said hollow spindle, means for defining a rim on said quill, an annular spring washer abutting one of said bearings and said rim for urging said enlargements out of said chamber and into said hollow spindle and for resiliently deflecting said fingers when said quill is moved axially of said spindle, a cover overlying said rim and slidable in said housing between positions axially spaced from said rim and in abutment with said rim, said cover being effective to move said rim and said quill axially to deform said spring washer and to move said enlargements axially and radially into said chamber, and means defining inclined tips on said fingers adapted to engage said step.

3. A dental handpiece construction as in claim 2 including means on said plunger top and engaging said detachable carrier top of said housing for limiting axial movement of said quill in said spindle.

* * * * *